US006682498B2

United States Patent
Ross

(10) Patent No.: US 6,682,498 B2
(45) Date of Patent: Jan. 27, 2004

(54) METHODS AND SYSTEMS FOR SUBCUTANEOUS GRAFT IMPLANTATION

(75) Inventor: John Ross, Bamberg, NC (US)

(73) Assignee: Vasca, Inc., Tewksbury, MA (US)

( * ) Notice: Subject to any disclaimer, the term of this patent is extended or adjusted under 35 U.S.C. 154(b) by 0 days.

(21) Appl. No.: 09/816,629

(22) Filed: Mar. 22, 2001

(65) Prior Publication Data
US 2002/0138031 A1 Sep. 26, 2002

(51) Int. Cl.⁷ .......................... A61M 37/00; A61M 3/00; A61M 25/00; A61M 5/00
(52) U.S. Cl. .................. 604/4.01; 604/43; 604/264
(58) Field of Search ........................ 604/4.01

(56) References Cited

U.S. PATENT DOCUMENTS

| | | | |
|---|---|---|---|
| 4,181,132 A | 1/1980 | Parks | |
| 4,309,994 A | * 1/1982 | Grunwald | ............ 604/28 |
| 4,892,518 A | 1/1990 | Cupp et al. | |
| 5,041,098 A | 8/1991 | Loiterman et al. | |
| 5,053,901 A | 10/1991 | Yamada et al. | |
| 5,203,771 A | 4/1993 | Melker et al. | |
| 5,215,530 A | 6/1993 | Hogan | |
| 5,234,406 A | 8/1993 | Drasner et al. | |
| 5,281,199 A | 1/1994 | Ensminger et al. | |
| 5,417,656 A | 5/1995 | Ensminger et al. | |
| 5,562,617 A | 10/1996 | Finch, Jr. et al. | |
| 5,713,859 A | 2/1998 | Finch, Jr. et al. | |
| 5,718,692 A | * 2/1998 | Schon et al. | ............ 604/264 |
| 5,755,780 A | 5/1998 | Finch, Jr. et al. | |
| 5,800,375 A | * 9/1998 | Sweezer et al. | ........ 604/101.05 |
| 5,807,356 A | 9/1998 | Finch, Jr. et al. | |
| 5,843,154 A | * 12/1998 | Osypka | ............ 607/122 |
| 5,931,829 A | * 8/1999 | Burbank et al. | ............ 604/264 |
| 5,984,908 A | * 11/1999 | Davis et al. | ............ 604/524 |
| 6,007,516 A | 12/1999 | Burbank et al. | |

* cited by examiner

Primary Examiner—Sang Y. Paik
Assistant Examiner—Filip Zec
(74) Attorney, Agent, or Firm—Townsend and Townsend and Crew LLP

(57) ABSTRACT

The present invention provides improved methods for establishing vascular access to a patient's body lumen or other target location, particularly blood vessels, for performing extracorporeal treatments, such as hemodialysis, hemofiltration, hemodiafiltration, plasmapheresis, apheresis, and the like, on circulating blood. In particular, the present invention provides improved methods which may enhance extracorporeal blood flow rates, reduce instances of fibrin sheath or thrombosis formation, and minimize recirculation effects. Methods for recirculating blood to a patient include placing a draw catheter so that a distal tip thereof is positioned in a right atrium of the patient's heart. A return catheter is placed so that a distal tip thereof is positioned in a superior vena cava. Extracorporeal blood flow from the draw catheter to the return catheter may then be established.

21 Claims, 9 Drawing Sheets

METHODS AND SYSTEMS FOR SUBCUTANEOUS GRAFT IMPLANTATION

BACKGROUND OF THE INVENTION

1. Field of the Invention

The present invention relates generally to medical methods. More particularly, the present invention provides improved methods, apparatus, and kits for establishing access to a patient's vascular system for hemodialysis and other extracorporeal blood treatments.

Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for relatively short procedures, such as intravenous feeding, intravenous drug delivery, and the like, they are not suitable for hemodialysis, hemofiltration, or other extracorporeal procedures that must be repeated periodically, often for the lifetime of the patient.

For hemodialysis and other extracorporeal treatment regimens, a variety of transcutaneous catheters and implantable ports have been proposed over the years. Transcutaneous catheters, such as the Tesio catheter available from Med Comp and the Perm-Cath™ available from Quinton, comprise a single catheter tube having a distal end placed in a vein in an in-dwelling manner and a proximal end which extends through the skin and which is available for connection to a hemodialysis or other blood treatment system.

Implantable ports, in contrast, are entirely subcutaneous and connect to a vein or an artery by a subcutaneous "connecting" cannula. Access to the port is achieved by percutaneous placement of a needle or other connecting tube. Such ports typically comprise a needle-penetrable septum to permit percutaneous penetration of the needle. Recently, several valved-port designs have been proposed, where percutaneous introduction of a needle or other access tube into the port opens the valve to permit flow to or from the cannula which connects to the blood vessel.

While both port-access and transcutaneously implanted cannula systems have enjoyed varying levels of success, they continue to suffer from certain disadvantages and limitations. For example, placement of both the port-access and transcutaneously implanted cannula systems has been problematic. Methods and systems for establishing vascular access have been described in related co-pending applications Ser. Nos. 09/333,828; 09/333,728; and 08/856,641, now U.S. Pat. No. 5,931,829, assigned to the assignee of the present application. Typically, such systems place a draw catheter, to draw blood out of the body, proximally of a return catheter, which returns treated blood to the body. Both catheters may be placed through the superior vena cava with the draw catheter tip in the superior vena cava and the return catheter tip extending to a junction between the superior vena cava and the right atrium. However, such access protocols can occasionally result in recirculation of returned treated blood back into the draw catheter. Additionally, such access methods permit only limited blood flow rates. Such limited blood flow rates are problematic since they prolong the duration of the associated extracorporeal blood treatment protocol, such as hemodialysis, hemofiltration, plasmapheresis, apheresis, and the like. Moreover, limited flow rates may cause possible catheter blockage or plugging resulting from fibrin sheath or thrombosis formation over the distal end of the catheter.

For these reasons, it would be desirable to provide improved methods for establishing access to a patient's vascular system for hemodialysis and other extracorporeal blood treatments. In particular, it would be desirable if such improved methods could provide enhanced flow rates without increasing a lumen diameter of the catheters, reduce instances of fibrin sheath or thrombosis formation, and minimize the recirculation of already treated blood. It would be further desirable if such improved methods were useful with both port-access and transcutaneous access systems for hemodialysis, hemofiltration, and other extracorporeal treatment systems. At least some of these objectives will be met by the methods of the present invention described hereinafter.

2. Description of the Background Art

U.S. Pat. No. 5,718,692 describes a double catheter assembly where each catheter has side holes at its distal end. U.S. Pat. Nos. 5,562,617 and 5,041,098 are exemplary of implantable systems employing cannulas extending between a port and a blood vessel for providing extracorporeal circulation. U.S. Pat. Nos. 5,417,656 and 5,281,199 show implantable ports which are connected to vascular cannulas via a transition region (FIG. 1A) and to a multiple branch cannula (FIG. 21). U.S. Pat. No. 4,892,518 shows an implanted port with a transition region extending to a cannula. U.S. Pat. Nos. 5,234,406 and 5,215,530 show two-piece catheters having a distal portion which can be placed percutaneously. The '406 patent discloses a large diameter proximal portion to enhance the flow rate of anesthetics to the subarachnoid region of the spine. U.S. Pat. Nos. 5,203,771 and 4,181,132 show implantable connectors which provide for percutaneous access to implanted shunts.

Related co-pending applications, assigned to the assignee of the present application, include Ser. Nos. 09/630,362; 09/333,828; 09/333,728; 09/238,523; 08/942,990, now U.S. Pat. No. 6,007,516; 08/856,641, now U.S. Pat. No. 5,931,829; 08/745,903, now U.S. Pat. No. 5,755,780; 08/724,948, now U.S. Pat. No. 6,053,901; 08/634,634, now U.S. Pat. No. 5,713,859; 08/539,105, now U.S. Pat. No. 5,807,356; and 60/036,124.

The full disclosures of each of the U.S. patents and co-pending applications listed above are hereby incorporated herein by reference.

SUMMARY OF THE INVENTION

The present invention provides improved methods for establishing vascular access to a patient's body lumen or other target location, particularly coronary blood vessels and cavities, for performing extracorporeal treatment on circulating blood. Exemplary extracorporeal treatment procedures include hemodialysis, hemofiltration, hemodiafiltration, plasmapheresis, apheresis, and the like. In particular, the present invention provides improved methods and kits which enhance extracorporeal blood flow rates, reduce instances of fibrin sheath or thrombosis formation, and minimize recirculation effects. The present invention is most advantageous with access systems comprising a pair of implantable ports connected to a pair of connecting catheters, usually a draw catheter and a return catheter. Specifically, one of the connecting catheters will be intended as a "draw" catheter for removing blood from the patient's vasculature while the other of the catheters will be intended as a "return" catheter for returning treated blood to the patient.

According to a first aspect of the present invention, methods for recirculating blood to a patient generally comprise placing a draw catheter so that a distal tip thereof is positioned in a right atrium of the patient's heart. A return catheter is placed so that a distal tip thereof is positioned in a superior vena cava. Extracorporeal blood flow from the draw catheter to the return catheter may be established. Such methods are particularly useful in that they enhance extracorporeal blood flow rates by placing the draw catheter in the right atrium so that the pressure in the right atrium assists to draw increased volumes of blood through the draw lumen. Such high volume extracorporeal treatment protocols typically provide extracorporeal blood flow rates above 200 ml/minute, usually rates above 300 to 350 ml/minute, and preferably rates above 400 ml/minute or higher. Moreover, the increased blood flow resulting from the increase in pressure (provided by the right atrium) serves to wash a distal tip of the draw catheter which in turn reduces the occurrence of fibrin sheath or thrombosis formation from completely occluding the tip of the catheter, and thereby reducing the risk of trauma.

The placement steps preferably comprise passing the draw catheter and the return catheter both into the superior vena cava, with the draw catheter extending beyond a distal end of the return catheter. A draw lumen is disposed at a distal end of the draw catheter. The draw lumen will typically be disposed distally of the distal end of the return catheter by a distance in the range from 5 cm to 10 cm, preferably being in the range from 5 cm to 8 cm, and more preferably by a distance of 6 cm. Such access protocols of placing the draw catheter distal of the return catheter in the right atrium prevents and/or minimizes recirculation of returned treated blood as the drawn blood is now returned to a location in the superior vena cava. This in turn increases the efficacy in performing extracorporeal treatment on circulating blood.

The draw catheter and the return catheter may generally comprise tubular bodies having substantially uniform diameters over their entire lengths. Usually, the tubular bodies of the catheters will comprise elastomeric materials, such as latex, silicone rubber, polyurethane, or the like. The catheters will usually (but not necessarily) have a uniform inside diameter along their entire length, typically being in the range from 1 mm to 15 mm, usually being in the range from 2 mm to 5 mm. The lengths of the catheters will usually be in the range from 15 cm to 100 cm, preferably being in the range from 20 cm to 40 cm. While it is preferred that each of the two or more catheters be identical in all respects, in order to simplify manufacturing and maintenance, the catheters may also be non-identical. For example, the cannulas may comprise different distal end configurations, as described in more detail below, or alternatively may have different lengths. Either or both of the catheters may also be trimmed to length during implantation so that each of the catheters is sufficiently long for the intended use.

Both ends of each of the draw and return catheters should also be adapted in all respects for implantation within the blood vessel or other target body lumen or location. For example, it is strongly preferred that the distal ends of each of the catheters be chamfered or beveled in order to reduce the risk of trauma when implanted within a blood vessel. In this way, both ends of each catheter are ready for implantation within a blood vessel without modification or other preparations. Furthermore, the distal end of either or both the draw catheter and the return catheter may be modified to have flow diffusers. For example, a plurality of side holes may be formed integrally or otherwise formed in or attached to the catheter at or near the end. Optionally, the end portion may be modified to form a single back hole or "backeye"

configuration. Still further, the end portion may be modified to form a V shaped end or "fish mouth" configuration. Such flow diffuser configurations serve to maintain flow if the distal tip of the draw or return catheter is positioned against the wall of the blood vessel or other target location. Additionally, the end portions of either or both of the catheters can be angled in order to further minimize the impact of fibrin sheath or thrombosis formation from completely occluding the tip of the catheter, thereby reducing the risk of trauma when implanted in a blood vessel.

The draw and return catheters may be formed together over at least a portion of their lengths so as to form a dual lumen catheter. Alternatively, the draw catheter and return catheter may be separately formed over their entire lengths so as to form two single lumen catheters. Additionally, proximal portions of either or both the draw catheter and the return catheter may have intermittent moveable rings. These intermittent rings about the catheters usually provide accurate placement of subcutaneous cuffs which become ingrown in tissue for permanent or temporary fixations of such access systems.

The establishing extracorporeal blood flow step preferably comprises percutaneously accessing a pair of implanted ports which are connected to the draw catheter and the return catheter. Usually, each port includes an inlet aperture adapted to receive an access tube and an outlet connector. The outlet connector on each port will usually comprise a male fitting so that the draw or return catheter may simply be placed over the fitting. The placement steps may occur either before or after the catheters are connected to the ports. Alternatively, extracorporeal blood flow may be established by connecting transcutaneous proximal portions of the draw catheter and return catheter to an external pump, or to other external catheters (which may optionally have different sizes, characteristics, etc.) for transcutaneous access.

In another aspect of the present invention, an improved method for recirculating blood to a patient generally comprises passing a draw catheter and a return catheter into a superior vena cava. The draw catheter is placed beyond a distal end of the return catheter for establishing extracorporeal blood flow from the draw catheter to the return catheter. In such a configuration, the distal end of the draw catheter is disposed distally of the distal end of the return catheter by a distance in the range from 5 cm to 10 cm.

The present invention further includes kits comprising a draw catheter, a return catheter, and instructions to use the draw catheter and the return catheter to recirculate blood to a patient. Instructions for use will generally recite the steps for performing one or more of the above described methods. The instructions will often be printed, optionally being at least in-part disposed on packaging. The instructions may alternatively comprise a videotape, a CD-ROM or other machine readable code, a graphical representation, or the like showing any of the above described methods. The kit components will be packaged in a conventional medical device package that is usually sterile, such as a pouch, tray, tube, box, or the like.

DESCRIPTION OF THE SPECIFIC EMBODIMENTS

The present invention provides improved methods for establishing vascular access to a patient's body lumen or other target location, particularly coronary blood vessels and cavities, for performing extracorporeal treatment on circulating blood. In particular, the present invention provides improved methods which may enhance extracorporeal blood flow rates, reduce instances of fibrin sheath or thrombosis formation, and minimize recirculation effects.

The present invention provides methods for facilitating both percutaneous and transcutaneous access. For percutaneous access, ports are implanted subcutaneously so that a passage therein lies a short distance beneath the surface of the patient's skin, typically being within 3 mm to 20 mm of the skin's surface. An access tube may then be percutaneously inserted into the passage in the access port in order to provide a connection to the blood vessel via the access port. For transcutaneous access, a catheter according to the present invention is implanted through the patient's skin with a distal end in the target blood vessel and a proximal end of the catheter adapted for connection to an external catheter. In both cases, access can be provided for a variety of purposes, usually involving withdrawal of blood, the extracorporeal treatment of the withdrawn blood, and/or the return of the treated blood to the patient. Such extracorporeal blood treatment will most often be for hemodialysis, but can also be for hemofiltration, hemodiafiltration, plasmapheresis, apheresis, and the like. In addition to extracorporeal treatment, the present invention can also be used for perfusing drugs, fluids, and other materials directly into a patient's circulation for a variety of purposes.

Figure 1:
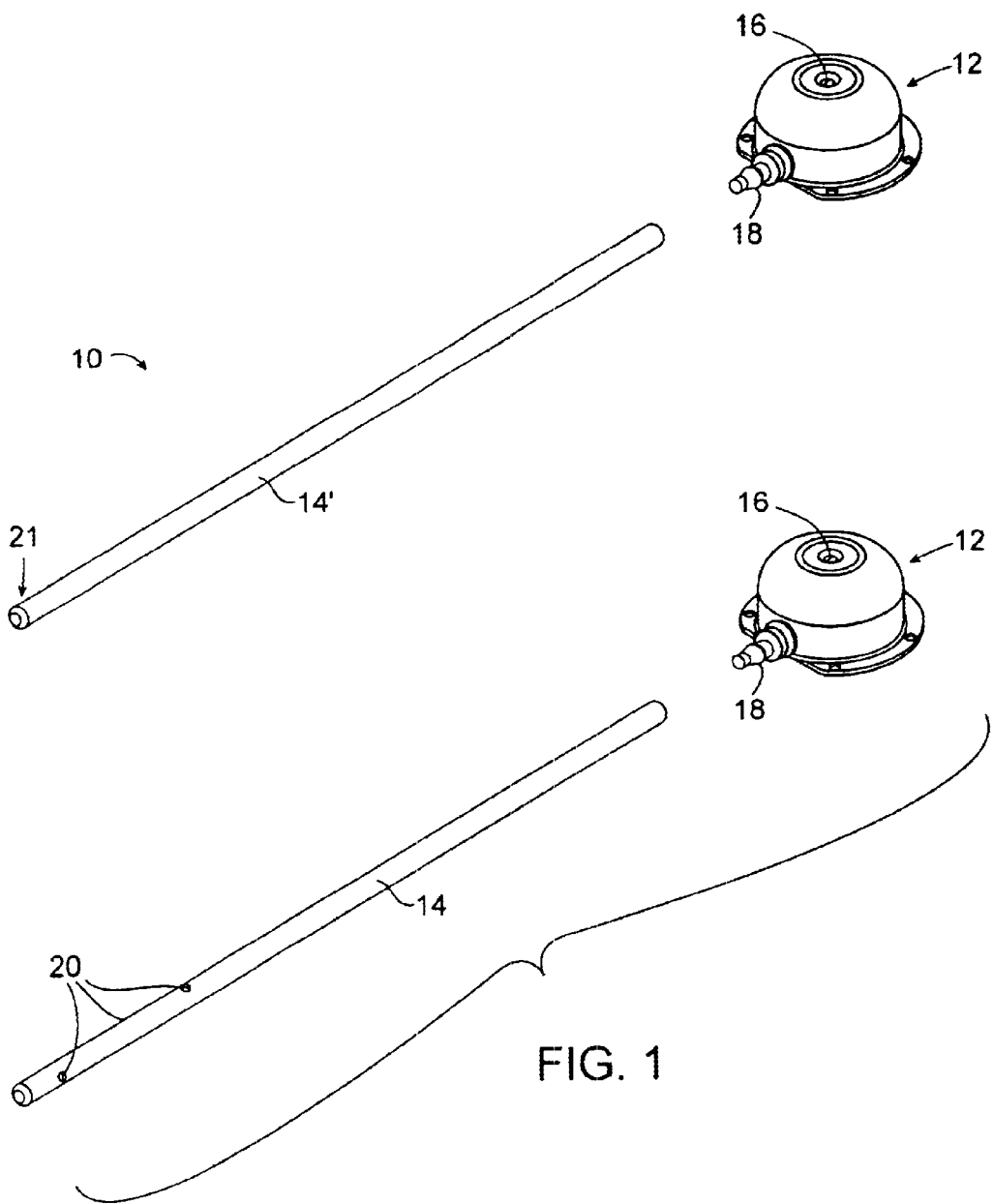
FIG. 1 is a isometric view of an exemplary access system that may be employed with the improved methods of the present invention which comprises a pair of implantable ports and a pair of connecting catheters.

Referring now to FIG. 1, an access system 10 that may be employed with the improved methods of the present invention will usually comprise one or more implantable ports 12, one draw catheter 14, and one return catheter 14'. The ports 12 are subcutaneously implantable and provide for percutaneous access by means of a needle or other access tube which is introduced through the patient's skin into an inlet aperture 16 on the top of the port. The port will also include an outlet connector 18, typically a male fitting, which is intended to attachably receive an end of the draw 14 or return 14' catheter. While the illustrated ports 12 include internal valves which open and close in response to insertion of the access tube through the aperture 16, as described in detail in co-pending application Ser. No. 08/942,990, now U.S. Pat. No. 6,007,516, the full disclosure of which is incorporated herein by reference, the present invention may also utilize a wide variety of ports having other valve structures, membrane-access structures, and other means for permitting an access tube to connect to a flow path defined by the outlet connector 18. It will be appreciated that the following depictions are for illustration purposes only and does not necessarily reflect the actual shape, size, or dimensions of the access device 10. This applies to all depictions hereinafter.

The draw catheter 14 and the return catheter 14' will comprise tubular bodies, typically fabricated by extruding biocompatible polymeric materials, such as silicone rubber, latex, polyurethane, polytetrafluoroethylene (PTFE), and the like. The draw catheter 14 and the return catheter 14' will have lengths, lumen diameters, and other dimensions as generally set forth above. Preferably, each of the catheters 14 and 14' will comprise tubular bodies having a uniform luminal diameter, more preferably a uniform luminal and outside diameter over the entire length. Also preferably, distal ends of the catheters 14 and 14' will be chamfered, rounded, beveled, or radiused so that the distal end may be placed into a blood vessel with reduced risk of trauma. The chamfer is typically at 45° relative to the axial direction, but could vary between 10° and 80°, usually 25° and 75°.

Figure 2A:
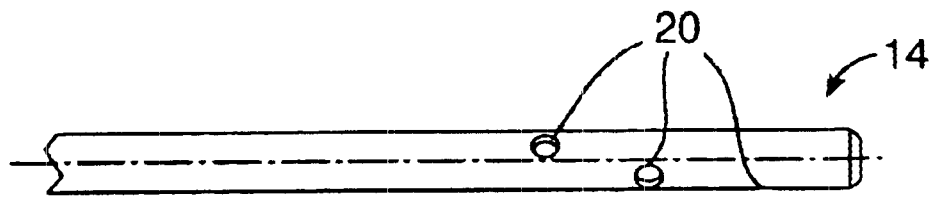
FIGS. 2A–2D illustrate an exemplary connecting catheter having flow diffusers in the form of side holes.
Figure 2B:
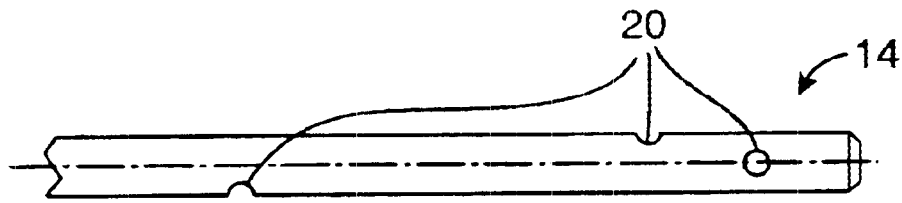
Figure 2C:
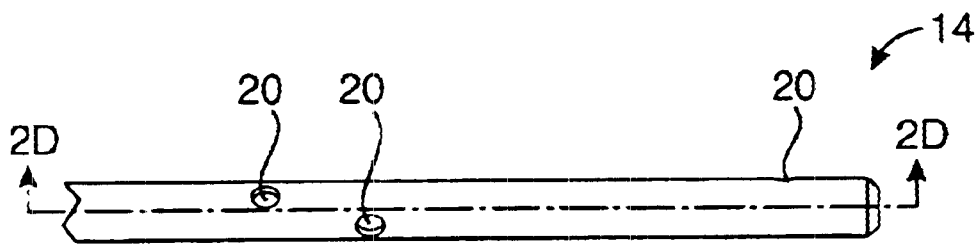
Figure 2D:
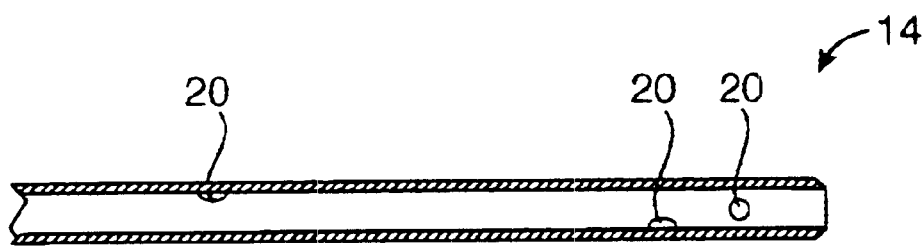
Figure 3A:
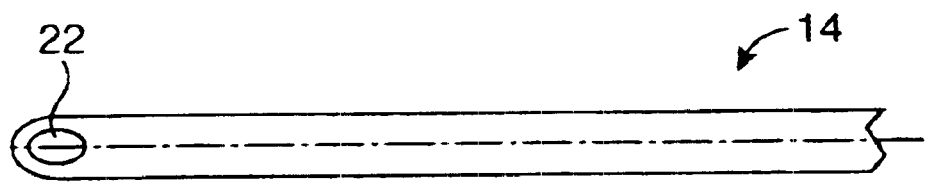
FIGS. 3A–3D illustrate an alternate embodiment of the connecting catheter having flow diffusers in the form of a back hole.
Figure 3B:
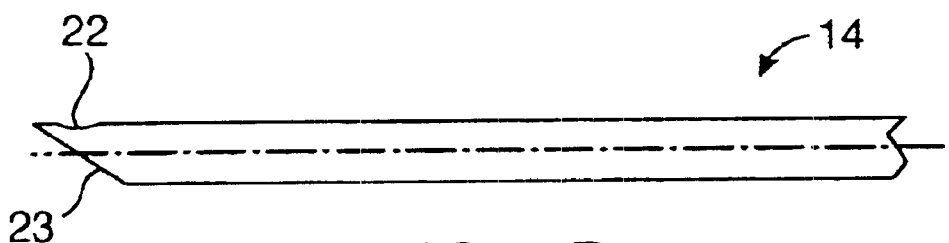
Figure 3C:
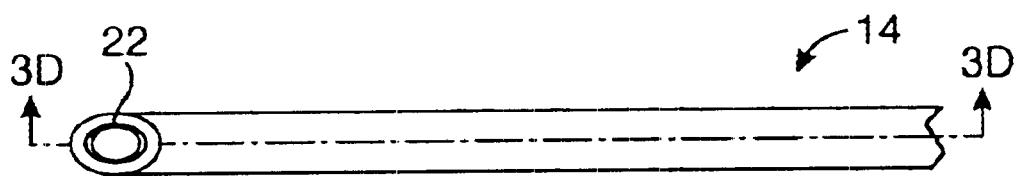
Figure 3D:
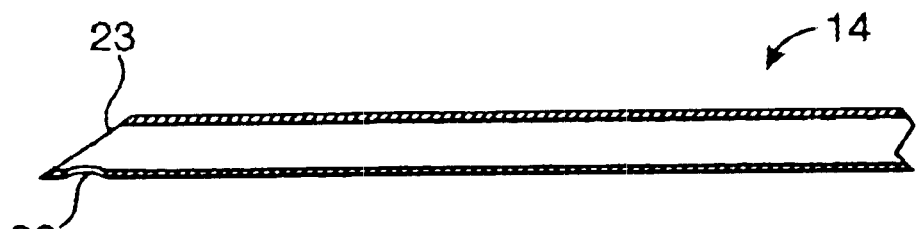
Figure 4A:
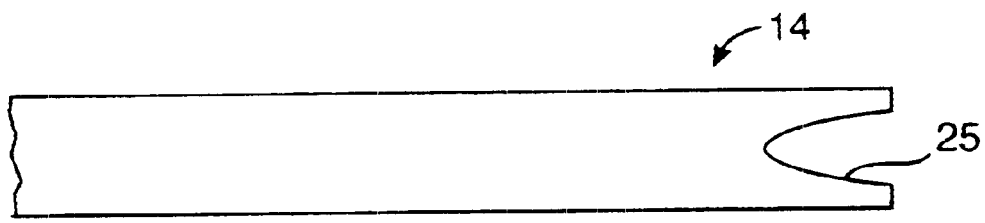
FIGS. 4A–4C illustrate an alternate embodiment of the connecting catheter having flow diffusers in the form of a V shaped end.
Figure 4B:
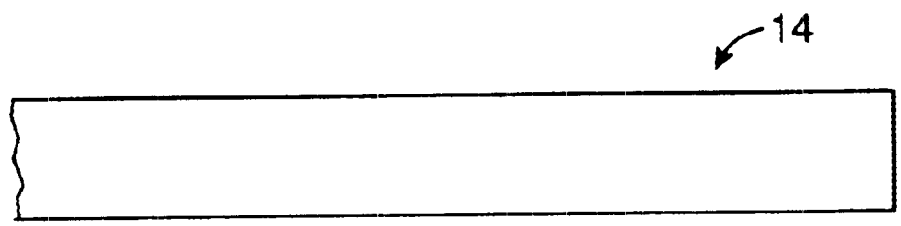
Figure 4C:
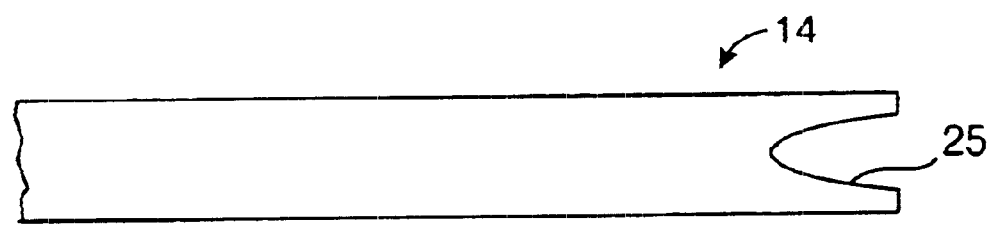

The distal ends of either or both the draw catheter 14 and the return catheter 14' may be modified to have flow diffusers. For example, one modification may comprise side holes 20 which extend over one end portion of the tubular body of the catheter as best observed in FIGS. 2A–2D. In this embodiment, side holes 20 extend in a spiral pattern over a length of the catheter in the range from 1 cm to 60 cm, usually from 2 cm to 40 cm. FIGS. 2A–2D illustrate the same catheter, with the catheter being rotated 90° about its axis in each of the four views, with FIG. 2D showing a cross section of the catheter along lines 2D—2D. FIGS. 3A–3D illustrate an alternate embodiment of the connecting catheter having flow diffusers in the form of a back hole 22. The back hole or "back eye" configuration 22 has a generally oval shape that extends on a distal portion of an angled end 23. FIGS. 4A–4C illustrate a still further modified portion of the connecting catheter having flow diffusers in the form of a V shaped or "fish mouth" end 25. An "unmodified" end 21 of each catheter 14, 14' may be plain or have a simple chamfer or radiused end, as shown in FIG. 1. This unmodified end is presently preferred as the return catheter 14'.

Figure 5:
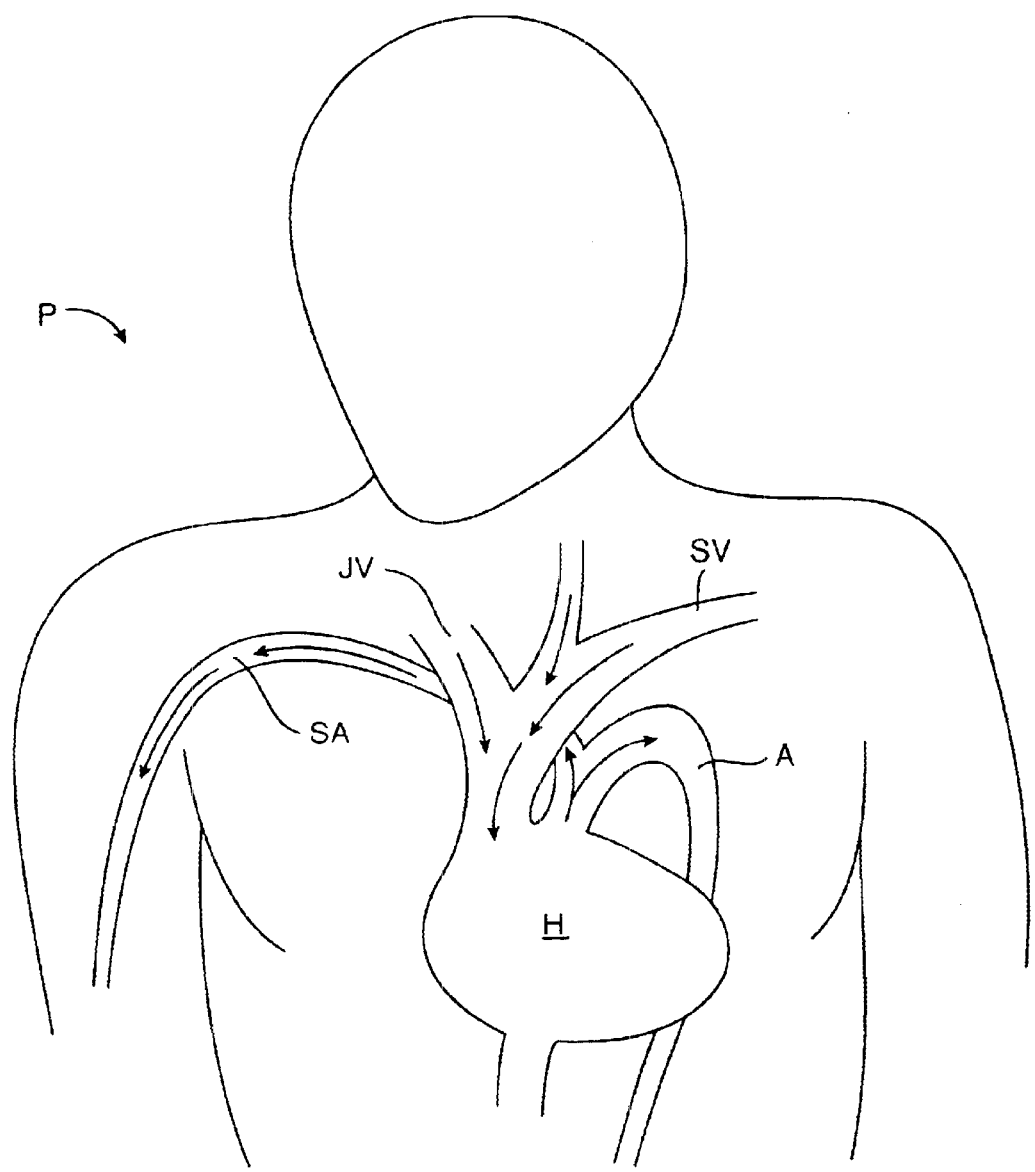
FIG. 5 illustrates a patient's vasculature to which the implantable access system of FIG. 1 may be attached.

The access systems described above are particularly suitable for establishing percutaneous and transcutaneous access to locations in the patient's vasculature, including both the arterial and venous vasculature. As illustrated in FIG. 5, the arterial and venous vasculature of patient P in the region immediately surrounding the heart H includes the jugular vein JV, the subclavian vein SV, the subclavian artery SA, and the aorta A.

Figure 6A:
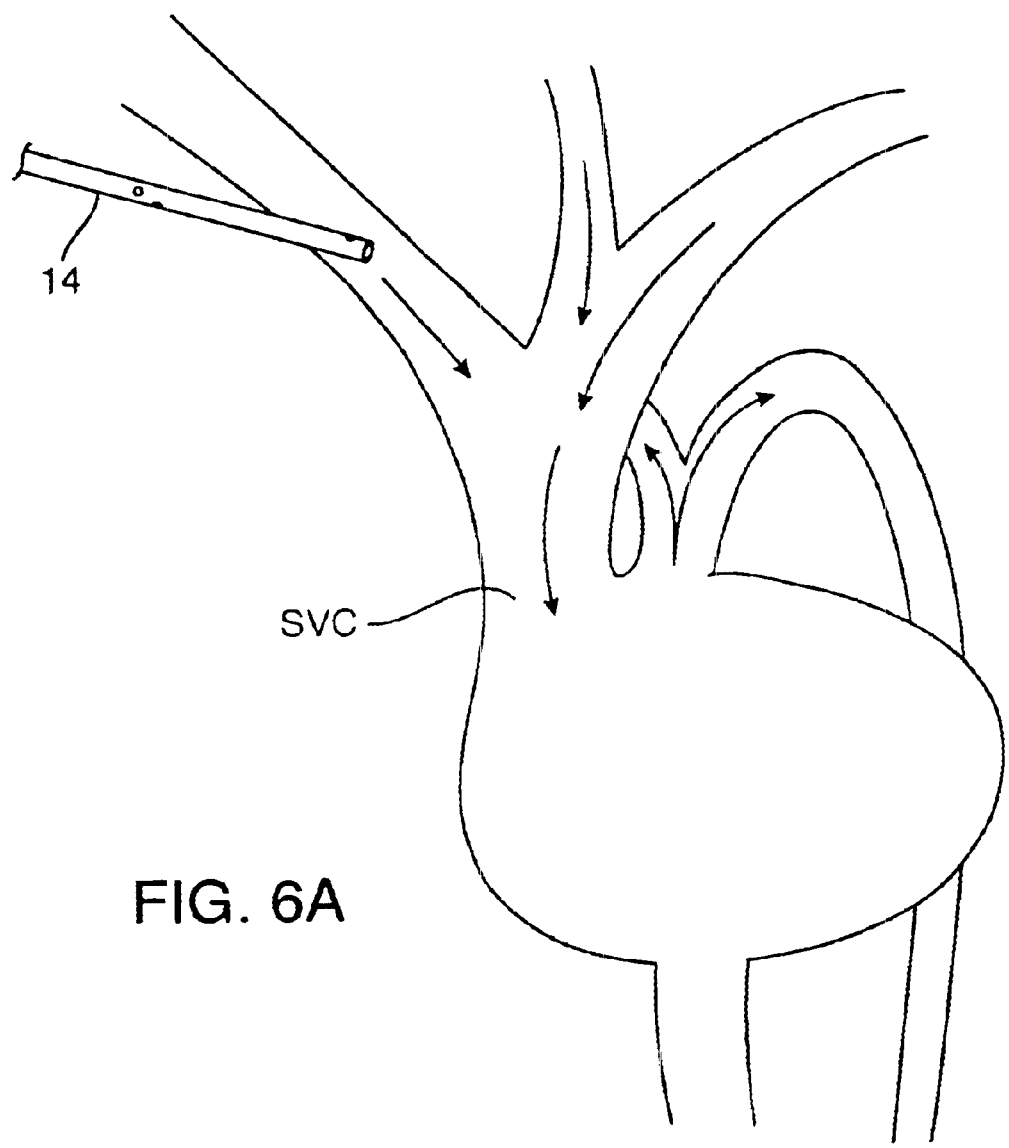
FIGS. 6A and 6B illustrate implantation of the connecting catheters according to the methods of the present invention.
Figure 6B:
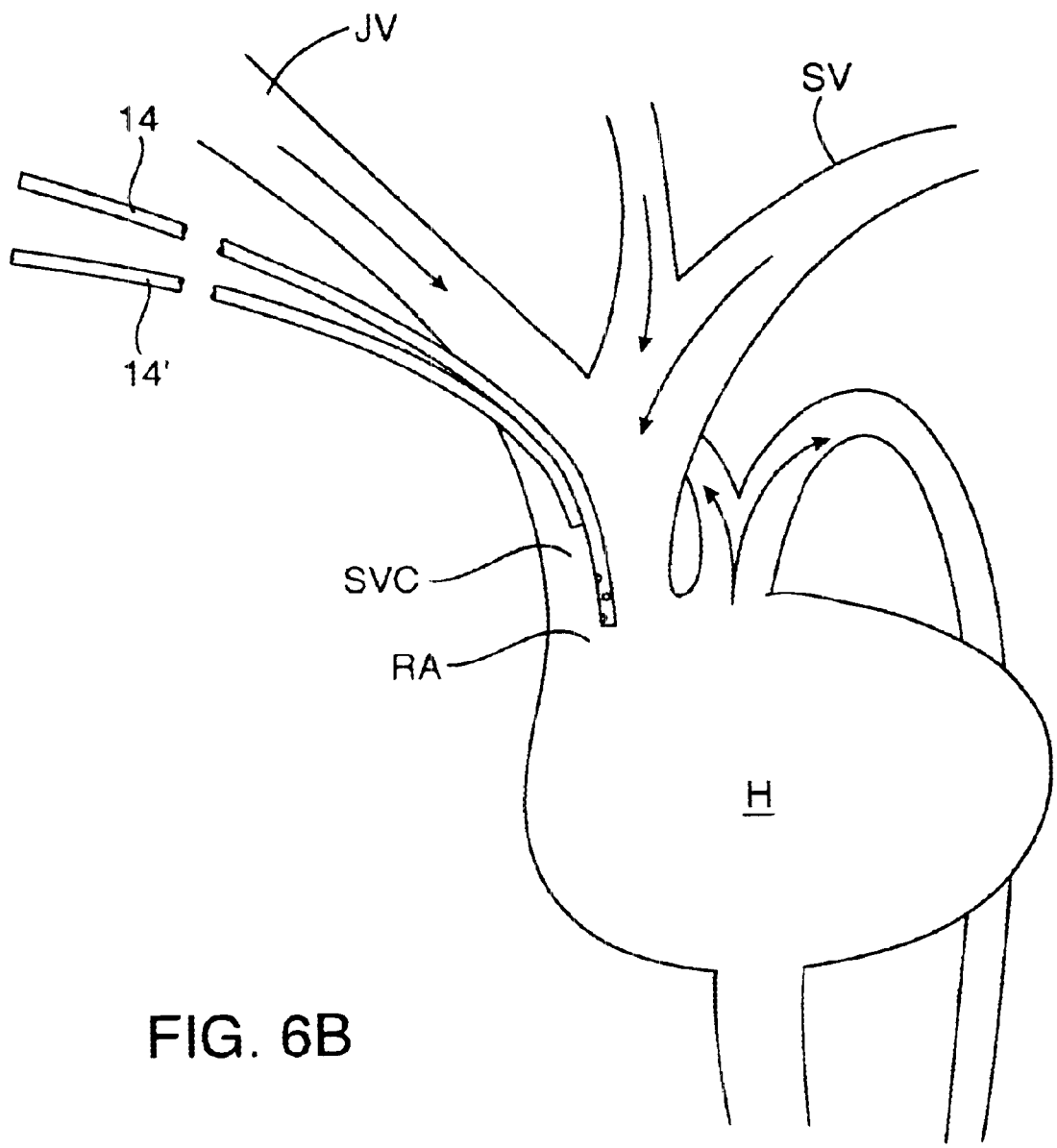

Referring now to FIGS. 6A and 6B, the implantation of the draw and return catheters 14, 14' for recirculating blood to a patient will be described. The catheters 14, 14' may be implanted by either a cut-down procedure or by the Seldinger technique. For simplicity, only the cut-down procedure will be described. After appropriately preparing and anesthetizing the patient, a small venotomy is performed at the desired site in the jugular vein JV, typically from 5 cm to 10 cm above the junction of the superior vena cava SVC and the right atrium of the heart H. The distal tip of the draw catheter 14 is then inserted through the incision in the vascular wall with an end having side holes 20 therein positioned so that a distal tip thereof is positioned in a right atrium RA of the patient's heart H. The return catheter 14' is positioned so that a distal tip thereof is positioned in a superior vena cava. Specifically, the draw catheter 14 and the return catheter 14' both pass into the superior vena cava, with the draw catheter 14 extending beyond a distal end of the return catheter 14'. The distal tip of the draw catheter 14 typically is disposed distally of the distal end of the return catheter 14' by a distance in the range from 5 cm to 10 cm, preferably being in the range from 5 cm to 8 cm, and more preferably by a distance of 6 cm. The positioning of the distal tips of the catheters 14, 14' may be verified by X-ray. Extracorporeal blood flow from the draw catheter 14 to the return catheter 14' may then be established.

As described above, such protocols enhance extracorporeal blood flow rates by placing the draw catheter in the right atrium so that the pressure in the right atrium assists to draw increased volumes of blood through the draw lumen. These high volume extracorporeal treatment protocols typically provide extracorporeal blood flow rates above 200 ml/minute, usually rates above 300 to 350 ml/minute, and preferably rates above 400 ml/minute or higher. Moreover, the increased blood flow serves to wash a distal tip of the draw catheter which in turn reduces the occurrence of fibrin sheath or thrombosis formation. Additionally, placing the draw catheter distal of the return catheter in the right atrium prevents and/or minimizes recirculation of returned treated blood as the drawn blood is now returned to a location in the superior vena cava.

At this point, the catheters 14, 14' may be prepared for transcutaneous use, i.e., where the proximal ends remain outside the patient's body available for connection to the desired extracorporeal recirculation system or pump. More usually, the catheters 14, 14', as shown in FIG. 7, will be connected to implantable ports 12. Placement of each of the ports 12 may be selected based on a number of criteria. The infraclavicular fossa is generally satisfactory, but the actual site may vary depending on the patient characteristics. The implantable ports 12 should be located in an anatomic area that provides for good stability, does not interfere with patient mobility, create pressure points, or interfere with clothing. Placement should allow for a proper amount of overlying cutaneous tissue, with an optimum tissue thickness in the range from 5 mm to 15 mm. Sufficient space should be available for placement of two implantable catheters.

After the port implantation site is selected, a subcutaneous pocket is formed by a cut-down procedure using blunt dissection. The pocket should be sufficiently large to accommodate the ports 12 and allow positioning of the ports away from the incision. After the pocket is created, a tunnel is created between the pocket and the venous entry site using a tunneling tool. The proximal ends of the catheters 14, 14' may then be cut to length so that they terminate at the venous entry site with sufficient slack for body movement and subcutaneous connection. The cut proximal ends of each catheter is then placed over the connector 18, and secured with a suture or other biocompatible filament. It will be appreciated that attachment of the catheters 14, 14' to their respective ports 12 may occur after implantation of the catheters, or the ports could be pre-connected to the catheters externally to the patient prior to implantation. In such cases, it will be desirable to premeasure the desired lengths of the catheters so that they may be precut to a selected length prior to attachment to the ports.

Figure 7A:
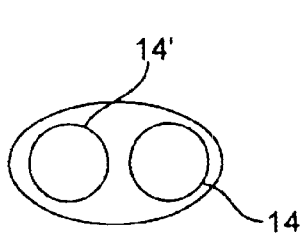
FIGS. 7A–7C illustrate the connecting catheters in a dual lumen configuration.
Figure 7B:
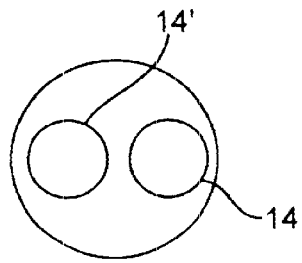
Figure 7C:
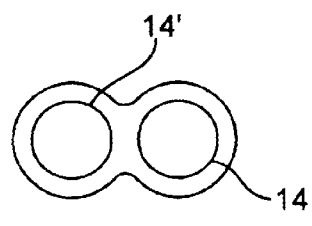
Figure 8:
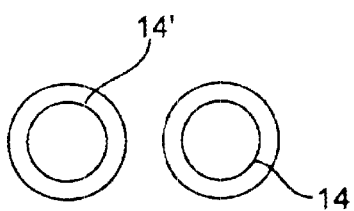
FIG. 8 illustrates the connecting catheters each having a single lumen.

Referring now to FIGS. 7A–7C, the draw and return catheters 14, 14' may be formed together over at least a portion of their lengths so as to form a dual lumen catheter. Alternatively, the draw catheter 14 and return catheter 14' may be separately formed over their entire lengths so as to form two single lumen catheters, as shown in FIG. 8.

Figure 9:
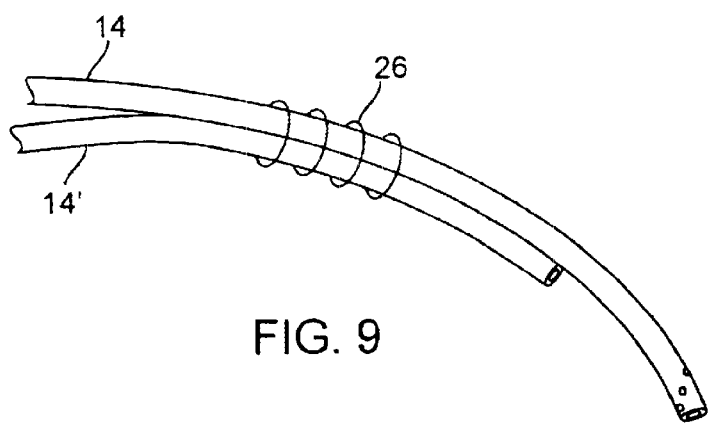
FIG. 9 illustrates movable rings attached to the proximal portions of the connecting catheters.

Referring now to FIG. 9, proximal portions of either or both the draw catheter 14 and the return catheter 14' may have intermittent moveable rings 26. These intermittent rings 26 about the catheters usually provide accurate placement of subcutaneous cuffs which become ingrown in tissue for permanent or temporary fixations of the access system 10.

Figure 10:
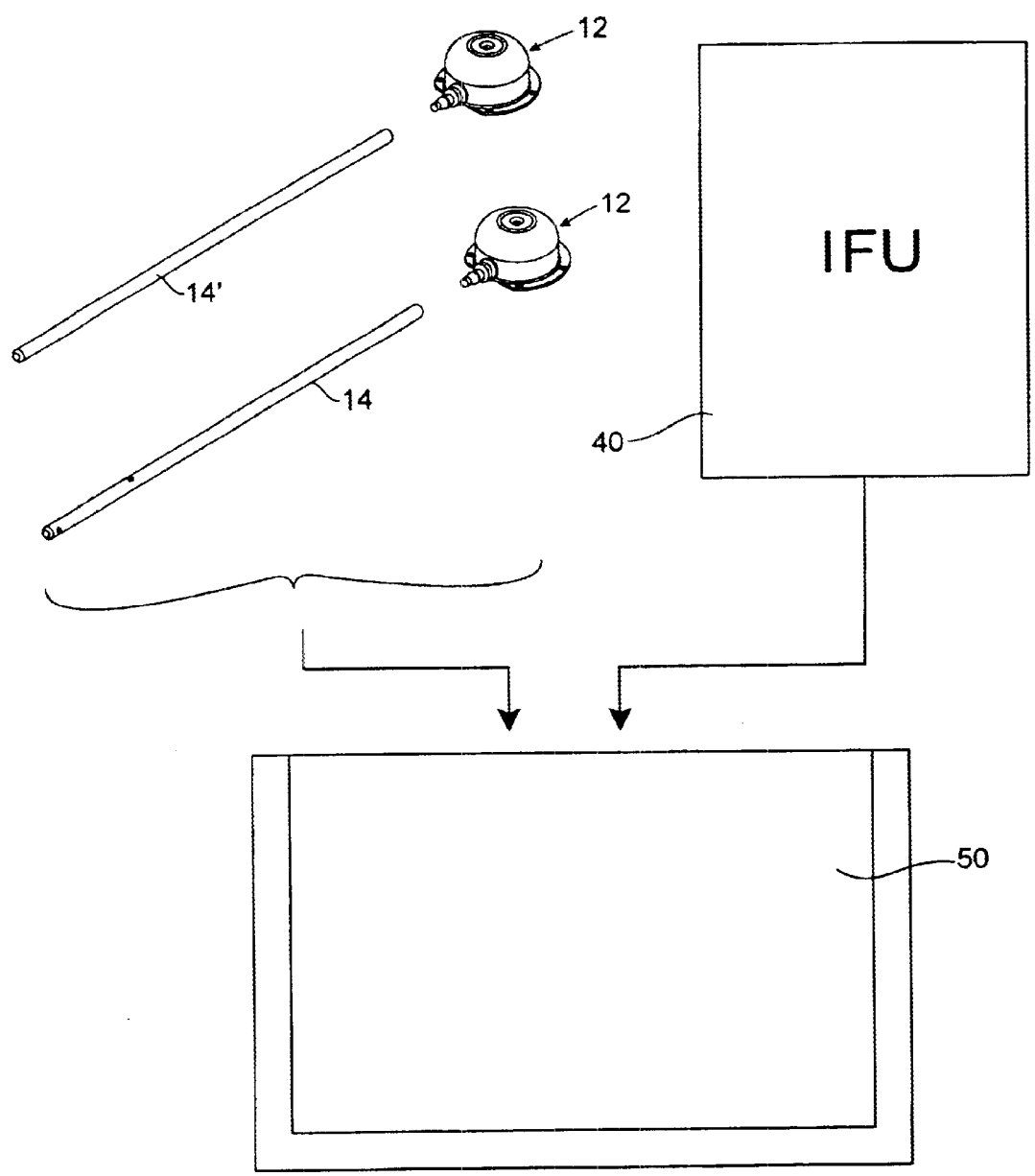
FIG. 10 illustrates a kit according the present invention comprising a pair of implantable ports, a pair of connecting catheters, instructions for use, and a package for holding all kit components.

Referring now to FIG. 10, kits according to the present invention will typically include a draw catheter 14, a return catheter 14', a pair of ports 12, and instructions 40 to use the draw catheter and the return catheter to recirculate blood to a patient. Instructions for use 40 will generally recite the steps for performing one or more of the above described methods. The instructions for use 40 will usually be printed on a separate sheet of paper (package insert), but may also be printed in whole or in part on other kit packaging. The instructions 40 may alternatively comprise a videotape, a CD-ROM or other machine readable code, a graphical representation, or the like showing any of the above described methods. The kit components will be packaged in a conventional medical device package that is usually sterile, such as a pouch 50, tray, tube, box, or the like.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A method for recirculating blood to a patient, said method comprising:

placing a draw catheter so that a distal tip thereof is positioned in a right atrium of the patient's heart; and placing a return catheter so that a distal tip thereof is positioned in a superior vena cava;

wherein extracorporeal blood flow from the draw catheter to the return catheter may be established;

wherein a draw lumen is disposed at a distal end of the draw catheter and wherein the draw lumen is disposed distally of a distal end of the return catheter by a distance between 5 cm to 10 cm.

2. A method as in claim 1, wherein the extracorporeal blood flow is established at a rate of at least 200 ml/min.

3. A method as in claim 1, wherein the extracorporeal blood flow is established at a rate of at least 400 ml/min.

4. A method as in any one of claims 1–3, wherein the draw catheter and the return catheter both pass into the superior vena cava, with the draw catheter extending beyond the distal end of the return catheter.

5. A method as in claim 4, wherein the draw lumen is disposed distally of the distal end of the return catheter by a distance of 6 cm.

6. A method as in claim 4, wherein the draw catheter and return catheter are formed together over at least a portion of their lenghts.

7. A method as in claim 4, wherein the draw catheter and return catheter are separately formed over their entire lengths.

8. A method as in claim 4, wherein the draw catheter and return catheter comprise elastomeric tubular bodies having substantially uniform diameters over their entire lenghts.

9. A method as in claim 8, wherein the distal end of the draw catheter is chamfered.

10. A method as in claim 8, wherein the distal end of the return catheter is chamfered.

11. A method as in claim 8, wherein the distal tip of the draw catheter comprises a plurality of side holes, a single back hole, or a V shaped end.

12. A method as in claim 8, wherein the distal tip of the return catheter comprises a plurality of side holes, a single back hole, or a V shaped end.

13. A method as in claim 8, wherein proximal portions of the draw catheter and the return catheter have intermittent moveable rings.

14. A method as in claim 4, wherein establishing extracorporeal blood flow comprises externally connecting transcutaneous proximal portions of the draw catheter and return catheter to an external pump.

15. A method as in claim 4, wherein establishing extracorporeal blood flow comprises percutaneously accessing implanted ports which are connected to the draw catheter and the return catheter.

16. An improved method for recirculating blood to a patient, wherein the improvement comprises passing a draw catheter and a return catheter into a superior vena cava and placing the draw catheter beyond a distal end of the return catheter for establishing extracorporeal blood flow from the draw catheter to the return catheter, wherein a distal end of the draw catheter is disposed distally of the distal end of the return catheter by a distance in a range from 5 to 10 cm.

17. An improved method as in claim 16, wherein the distal end of the draw catheter is placed in a right atrium of a patient's heart.

18. An improved method as in claim 16, wherein the distal end of the return catheter is placed in a superior vena cava.

19. A kit comprising:
   a draw catheter;
   a return catheter; and
   instructions to use the draw catheter and the return catheter to recirculate blood to a patient according to any of claims 1–3 or 16–18.

20. A method for recirculating blood to a patient, said method comprising:
   placing a draw catheter so that a distal tip thereof is positioned in a right atrium of the patient's heart; and
   placing a return catheter so that a distal tip thereof is positioned in a superior vena cava;
   wherein extracorporeal blood flow from the draw catheter to the return catheter may be established;
   wherein the draw catheter and the return catheter both pass into the superior vena cava, with the draw catheter extending beyond a distal end of the return catheter;
   wherein the draw catheter and return catheter comprise elastomeric tubular bodies having substantially uniform diameters over their entire lengths, wherein a distal end of the draw catheter is chamfered.

21. A method for recirculating blood to a patient, said method comprising:
   placing a draw catheter so that a distal tip thereof is positioned in a right atrium of the patient's heart; and
   placing a return catheter so that a distal tip thereof is positioned in a superior vena cava;
   wherein extracorporeal blood flow from the draw catheter to the return catheter may be established;
   wherein the draw catheter and the return catheter both pass into the superior vena cava, with the draw catheter extending beyond a distal end of the return catheter;
wherein the draw catheter and return catheter comprise elastomeric tubular bodies having substantially uniform diameters over their entire lengths, wherein the distal end of the return catheter is chamfered.

* * * * *